US006403821B1

(12) United States Patent
Pressman et al.

(10) Patent No.: US 6,403,821 B1
(45) Date of Patent: Jun. 11, 2002

(54) CATALYST COMPOSITION AND METHOD FOR PRODUCING DIARYL CARBONATES USING NITRILE AS PROMOTER

(75) Inventors: Eric James Pressman, East Greenbush; Grigorii Lev Soloveichik, Latham; Bruce Fletcher Johnson, Scotia; Kirill Vladimirovich Shalyaev, Clifton Park, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/677,179

(22) Filed: Oct. 2, 2000

Related U.S. Application Data

(62) Division of application No. 09/345,538, filed on Jun. 30, 1999.

(51) Int. Cl.[7] ............................ C07C 69/96; B01J 29/14
(52) U.S. Cl. ......................................... 558/274; 502/74
(58) Field of Search ............................. 558/274; 502/74

(56) References Cited

U.S. PATENT DOCUMENTS

| 1,102,566 A | 2/1914 | Clark et al. | |
| 4,187,242 A | 2/1980 | Chalk | |
| 5,380,907 A | 1/1995 | Mizukami et al. | ........... 558/270 |
| 5,498,789 A | 3/1996 | Takagi et al. | |
| 5,543,547 A | 8/1996 | Iwane et al. | ................ 558/274 |
| 5,726,340 A | 3/1998 | Takagi et al. | ................ 558/274 |

FOREIGN PATENT DOCUMENTS

EP 452997 A2 10/1991

*Primary Examiner*—Floyd D. Higel
*Assistant Examiner*—Ebenezer Sackey
(74) *Attorney, Agent, or Firm*—S. Bruce Brown; Noreen C. Johnson

(57) ABSTRACT

Hydroxyaromatic compounds such as phenol are carbonylated with oxygen and carbon monoxide in the presence of a catalyst system comprising a Group VIIIB metal, preferably palladium; an alkali metal or alkaline earth metal halide, preferably sodium bromide; and a promoter compound which is at least one $C_{2-8}$ aliphatic or $C_{7-10}$ aromatic mono- or dinitrile, preferably acetonitrile or adiponitrile. The catalyst system also preferably contains a compound of a non-Group VIIIB metal, preferably lead.

12 Claims, No Drawings

CATALYST COMPOSITION AND METHOD FOR PRODUCING DIARYL CARBONATES USING NITRILE AS PROMOTER

This application is a divisional of Ser. No. 09/345,538 filed Jun. 30, 1999.

BACKGROUND OF THE INVENTION

This invention relates to the preparation of diaryl carbonates by oxidative carbonylation. More particularly, it relates to the improvement of diaryl carbonate yield in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by an oxidative carbonylation (hereinafter sometimes simply "carbonylation" for brevity) reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is a Group VIIIB metal, i.e., a metal selected from the group consisting of ruthenium, rhodium, palladium, osmium, iridium and platinum, or a complex thereof.

A further development in the carbonylation reaction, including the use of compounds of other metals such as lead or cerium as cocatalysts, is disclosed in various patents including U.S. Pat. No. 5,498,789. Also required according to that patent is the use of quaternary ammonium or phosphonium halides, as illustrated by tetra-n-butylammonium bromide, as part of the catalyst package.

The commercial viability of the carbonylation reaction would be greatly increased if a less expensive compound could be substituted for the quaternary ammonium or phosphonium halide. It has been discovered, however, that substitution of such compounds as sodium bromide normally results in the isolation of the desired diaryl carbonate in low or insignificant yield.

In U.S. Pat. Nos. 5,543,547 and 5,726,340, the use of carbonylation catalyst systems including palladium or an analogous metal, various cocatalytic metals which may include cerium, lead or cobalt, and an alkali metal or quaternary ammonium bromide is disclosed. Also present may be materials characterized as inert solvents. These may be aliphatic or alicyclic hydrocarbons such as hexane, heptane or cyclohexane; chlorinated aliphatic hydrocarbons such as methylene chloride or chloroform; aromatic hydrocarbons such as toluene or xylene; chlorinated aromatic hydrocarbons such as chlorobenzene; ethers such as diethyl ether, diphenyl ether, tetrahydrofuran or dioxane; esters such as ethyl acetate or methyl formate; nitroaromatic compounds such as nitrobenzene; or acetonitrile. There is no suggestion, however, that yields of diaryl carbonate are in any way improved by the use of any of these "solvents" in a halide-containing catalyst package.

U.S. Pat. No. 5,380,907 discloses the use of a nitrile in combination with palladium and a manganese or copper cocatalyst. The result is an increase in yield, but yields are still too low to permit contemplation of commercial use for the disclosed catalyst systems.

It is of interest, therefore, to develop catalyst systems which include an inexpensive halide compound and which can efficiently produce diaryl carbonates.

SUMMARY OF THE INVENTION

The present invention provides a method for preparing diaryl carbonates which includes a relatively inexpensive halide and a promoter compound which maximizes the effectiveness of said halide. Also provided is a catalyst composition useful in such a method.

In one of its aspects, the invention is a method for preparing a diaryl carbonate which comprises contacting at least one hydroxyaromatic compound with oxygen and carbon monoxide in the presence of an amount effective for carbonylation of at least one catalytic material comprising:

(A) a Group VIIIB metal or a compound thereof, (B) at least one alkali metal halide, and (C) an amount effective to optimize diaryl carbonate formation of a promoter compound which is at least one $C_{2-8}$ aliphatic or $C_{7-10}$ aromatic mono- or dinitrile.

Another aspect of the invention is catalyst compositions comprising components A, B and C as described above, and any reaction products thereof.

DETAILED DESCRIPTION; PREFERRED EMBODIMENTS

Any hydroxyaromatic compound may be employed in the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonate oligomers.

Other essential reagents in the method of this invention are oxygen and carbon monoxide, which react with the phenol to form the desired diaryl carbonate. They may be employed in high purity form or diluted with another gas such as nitrogen, argon, carbon dioxide or hydrogen which has no negative effect on the reaction.

For the sake of brevity, the constituents of the catalyst system are defined as "components" irrespective of whether a reaction between said constituents occurs before or during the carbonylation reaction. Thus, the catalyst system may include said components and any reaction products thereof.

Component A of the catalyst system is one of the Group VIIIB metals, preferably palladium, or a compound thereof. Thus, useful palladium materials include elemental palladium-containing entities such as palladium black, palladium/carbon, palladium/alumina and palladium/silica; palladium compounds such as palladium chloride, palladium bromide, palladium iodide, palladium nitrate, palladium acetate and palladium 2,4-pentanedionate; and palladium-containing complexes involving such compounds as carbon monoxide, nitrites and olefins. Preferred in many instances are palladium(II) salts of organic acids, most often $C_{2-6}$ aliphatic carboxylic acids, and palladium(II) salts of β-diketones. Palladium(II) acetate and palladium(II) 2,4-pentanedionate are generally most preferred. Mixtures of the aforementioned palladium materials are also contemplated.

Component B is at least one alkali metal halide. The alkali metal bromides such as lithium bromide, sodium bromide and potassium bromide are preferred, with sodium bromide often being most preferred by reason of its particular suitability and relatively low cost.

Component C is a promoter compound, said compound being at least one $C_{2-8}$ aliphatic or $C_{7-10}$ aromatic mono- or dinitrile. Illustrative mononitriles are acetonitrile, propionitrile and benzonitrile; illustrative dinitriles are succinonitrile, adiponitrile and benzodinitrile. Mononitriles are generally preferred, with acetonitrile and adiponitrile being most preferred.

It should be noted that contrary to the suggestion of some of the prior art identified hereinabove, the function of component C in the present invention is not simply that of a solvent. Rather, the nitrite is an active catalyst constituent which improves the yield of the desired diaryl carbonate.

In a highly preferred embodiment of the invention, there is also present in the catalyst system (D) at least one cocatalyst which is a compound of a non-Group VIIIB metal, preferably one which is soluble in the liquid phase under the reaction conditions. Numerous other metal compounds are known in the art to be active as carbonylation cocatalysts, and any compound having such activity may be used according to the present invention provided an improvement in diphenyl carbonate production, usually yield, is achieved thereby.

Illustrative cocatalytic metals include cerium, titanium, cobalt, copper, zinc, manganese, iron and lead, which may be used singly or in combination. For the purposes of this invention the preferred cocatalysts are those containing metals other than Group VIII metals; that is other than iron, cobalt and nickel. More preferred are compounds of lead, particularly when used alone or in combination with titanium or cerium compounds. It should be noted, however, that component C is not effective to optimize diaryl carbonate formation for all possible permutations of component D; the combined effectiveness of the two for this purpose may be determined by simple experimentation.

Examples of lead compounds which may be employed are lead oxides such as PbO and $Pb_3O_4^-$; inorganic lead salts such as lead(II) nitrate; lead carboxylates such as lead(II) acetate, lead(II)propionate and lead(IV) acetate; lead alkoxides and aryloxides such as lead(II) methoxide and lead(II) phenoxide; and lead salts of β-diketones such as lead(II) 2,4-pentanedionate. Mixtures of the aforementioned lead compounds may also be employed. The preferred lead compounds are lead(II) oxide, lead(II) aryloxides and lead (II) 2,4-pentanedionate. The preferred compounds of other metals are, for the most part, salts of β-diketones and especially 2,4-pentanedionates.

In addition to the aforementioned reactants and catalyst system, it is strongly preferred for a desiccant to be present in the reaction system. The preferred desiccants are non-reactive materials such as molecular sieves, as illustrated by 3-Ångstrom (hereinafter "3A") molecular sieves. They are usually isolated from the other reactants, as by presence in a basket mounted to a stirrer shaft or the like.

Component A is most often present in the amount of about 0.1–100,000 ppm, preferably 1–1,000 ppm, of Group VIIIB metal based on hydroxyaromatic compound, and component B in the amount of about 1–2,000 gram-atom of total metal per gram-atom of palladium in component A. Component D, when employed, is generally present in the amount of about 1–100 gram-atoms of total metal per gram-atom of palladium in component A.

The role of component C in the composition and method of the invention is believed to be to increase the degree of dissociation and ionization of the halide anion of component B, perhaps by forming a complex with the cationic portion of said component, although the invention is in no way dependent on this or any other theory of operation. The amount of component C employed will be an amount effective to optimize diaryl carbonate formation, in general by increasing the yield of the desired diaryl carbonate as evidenced, for example, by an increase in "turnover number"; i.e., the number of moles of diaryl carbonate formed per gram-atom of palladium present. This amount is most often about 1 prat by weight of component C per 1–15, preferably about 1–6, parts of hydroxyaromatic compound.

The method of the invention is preferably conducted in a reactor in which the hydroxyaromatic compound and catalyst system are charged under pressure of carbon monoxide and oxygen and heated. The reaction pressure is most often within the range of about 1–500 and preferably about 1–150 atm. Gas is usually supplied in proportions of about 2–50 mole percent oxygen with the balance being carbon monoxide, and in any event, the mole percentage of oxygen used should be outside the explosion range for safety reasons. The gases may be introduced separately or as a mixture. Reaction temperatures in the range of about 60–150° C. are typical. In order for the reaction to be as rapid as possible, it is preferred to substantially maintain the total gas pressure and partial pressure of carbon monoxide and oxygen, as described, for example, in U.S. Pat. No. 99,734, until conversion of the hydroxyaromatic compound is complete.

The diaryl carbonates produced by the method of the invention may be isolated by conventional techniques. It is often preferred to form and thermally crack an adduct of the diaryl carbonate with the hydroxyaromatic compound, as described in U.S. Pat. Nos. 239,106 and 5,312,955.

The method of the invention is illustrated by the following examples. Minor variations in reagent amounts from one example to another are not believed significant from the standpoint of yield.

EXAMPLES 1–4

A constant composition gas flow reactor system, as disclosed in the aforementioned U.S. Pat. No. 5,399,734, was charged in each example with 61.1 g (649 mmol) of phenol, 4.9 mg of palladium (26 ppm based on phenol) as palladium (II) 2,4-pentanedionate, 205.4 mg of lead(II) oxide, 650 equivalents (based on palladium) of sodium bromide and various proportions of acetonitrile. Molecular sieves, 38 g, were placed in a perforated polytetrafluoroethylene basket mounted to the stir shaft of the reactor.

The reactor was sealed, pressurized to 89.8 atm with a mixture of 9.1 mole percent oxygen and 90.9 mole percent carbon monoxide and stirred as its temperature was increased to 100° C. over 10 minutes. Further oxygen-carbon monoxide mixture was introduced at a flow rate of 330 ml/min and a pressure of about 88.5–89.8 atm. Gas flow was continued for 2.5 hours, during which the reaction mixture was frequently analyzed by high pressure liquid chromatography.

The results are given in Table I, in comparison with eight controls. Turnover numbers are those observed at the point of highest diphenyl carbonate content of each reaction mixture, as shown by analysis.

TABLE 1

| Example | Component B | Component C or replacement identity | Phenol: component C (or replacement) wt. ratio | Turnover number |
|---|---|---|---|---|
| 1 | NaBr | Acetonitrile | 11.5 | 900 |
| 2 | NaBr | Acetonitrile | 5.25 | 2216 |
| 3 | NaBr | Acetonitrile | 3.17 | 2992 |
| 4 | NaBr | Acetonitrile | 1.08 | 2898 |
| Control 1 | TEAB | — | — | 5587 |
| Control 2 | TEAB | Acetonitrile | 2.81 | 4130 |
| Control 3 | NaBr | — | — | 626 |
| Control 4 | — | Acetonitrile | 2.83 | 385 |
| Control 5 | NaBr | Toluene | 2.33 | 385 |
| Control 6 | NaBr | Chlorobenzene | 2.23 | 375 |
| Control 7 | NaBr | Diphenyl ether | 2.45 | 535 |
| Control 8 | NaBr | Heptane | 2.45 | 760 |

It can be seen that the proportion of diphenyl carbonate produced, as shown by turnover number, is substantially higher for Examples 1–4 than for Controls 3 and 4 in which components C and B, respectively, were not employed, and also higher than for Controls 5–8 in which various other compounds, including aliphatic and aromatic hydrocarbons, chlorinated hydrocarbons and ethers, were employed in place of nitriles as component C. In fact, the results of Examples 1–4 are comparable in certain respects to Control 1, employing TEAB alone.

A comparison of Controls 1 and 2 shows that with TEAB, the presence of acetonitrile results in a decrease in turnover number, contrary to the comparison of Control 3 with Examples 1–4. Thus, it is unexpected and unpredictable that nitrites function as true promoters, not merely as solvents, when employed with sodium bromide.

EXAMPLE 5

The procedure of Examples 1–4 was repeated, omitting the lead(II) oxide. The results are given in Table II, in comparison with two controls.

TABLE II

| Example | Component B | Component C or replacement identity | Phenol: component C (or replacement) wt. ratio | Turnover number |
|---|---|---|---|---|
| 5 | NaBr | Acetonitrile | 3.12 | 357 |
| Control 9 | TEAB | — | — | 356 |
| Control 10 | NaBr | — | — | 131 |

Table II shows that in the absence of component D, the use of acetonitrile affords essentially the same results as the use of TEAB without acetonitrile, and substantially superior results to the use of sodium bromide without acetonitrile.

EXAMPLE 6

The procedure of Examples 1–4 was repeated, employing palladium(II) 2,4-pentanedionate at a level of 17 ppm based on phenol, sodium bromide at a level of 230 equivalents based on palladium, a mixture of lead(II) oxide and titanium (IV) oxide bis(2,4-pentanedionate) (57 and 4 equivalents, respectively, based on palladium), a pressure of 108.8 atm and a reaction time of 1.5 hours. Diphenyl carbonate was obtained at a turnover number of 5010.

EXAMPLES 7–8

Batch carbonylation experiments were conducted in glass reactor vessels, employing palladium(II) 2,4-pentanedionate, sodium bromide and adiponitrile at levels of 0.2 mmol of palladium per liter, 240 equivalents of sodium bromide per equivalent of palladium and 53.8% by volume adiponitrile based on phenol. Various cocatalyst combinations were employed as component D. The reaction vessels were pressurized to 81.6 atm with a mixture of 91.7 mole percent carbon monoxide and 8.3 mole percent oxygen and heated at 100° C. for 3 hours. The contents of the vessels were analyzed for diphenyl carbonate by vapor phase chromatography. The results are given in Table III. The abbreviation "acac" represents the 2,4-pentanedionate. Cocatalyst proportions are in moles of metal per gram-atom of palladium. The controls contained no nitrile but were otherwise similar in content.

TABLE III

| Example | Cocatalyst (moles) | Turnover number |
|---|---|---|
| 7 | CuII(acac)$_2$ (10)<br>TiIVO(acac)$_2$ (10) | 1316 |
| 8 | PbO (24)<br>CeIII/(acac)$_3$ (10) | 1081 |
| Control 9 | CuII(acac)$_2$ (10)<br>TiIVO(acac)$_2$ (10) | 364 |
| Control 10 | PbO (24)<br>CeIII/(acac)$_3$ (10) | 540 |

It can be seen that production of diphenyl carbonate using these cocatalysts in combination with sodium bromide was also substantially improved by the addition of the nitrile.

What is claimed is:

1. A catalyst composition comprising the following and any reaction products thereof:
   (A) a Group VIIIB metal or a compound thereof,
   (B) at least one alkali metal or alkaline earth metal halide, and
   (C) at least one promoter compound which is a $C_{2-8}$ aliphatic or a $C_{7-10}$ aromatic mono- or dinitrile.

2. A composition according to claim 1 further comprising (D) at least one cocatalyst which is a compound of a non-Group VIIIB metal.

3. A composition according to claim 1 wherein the Group VIIIB metal in component A is palladium.

4. A composition according to claim 3 wherein component A is palladium(II) acetate or palladium(II) 2,4-pentanedionate.

5. A composition according to claim 2 wherein component D is a compound of a metal other than a Group VIII metal.

6. A composition according to claim 5 wherein component D is lead(II) oxide.

7. A composition according to claim 1 wherein component C is an alkali metal bromide.

8. A composition according to claim 7 wherein component B is sodium bromide.

9. A composition according to claim 1 wherein component C is acetonitrile.

10. A catalyst composition comprising the following and any reaction products thereof:
    (A) palladium or a compound thereof,
    (B) sodium bromide,
    (C) acetonitrile and
    (D) at least one lead compound and optionally titanium or cerium compound.

11. The composition according to claim 1 wherein a desiccant is also present.

12. The composition according to claim 10 wherein a desiccant is also present.

* * * * *